(12) United States Patent
Campin et al.

(10) Patent No.: US 12,390,101 B2
(45) Date of Patent: Aug. 19, 2025

(54) MULTI-DETECTOR ANALYSIS OF THE TEAR FILM OF AN EYE

(71) Applicant: Alcon Inc., Fribourg (CH)

(72) Inventors: John Alfred Campin, Southlake, TX (US); Martin Gründig, Rangsdorf (DE); Daniil Nekrassov, Berlin (DE); George Hunter Pettit, Fort Worth, TX (US); Peter Zieger, Berlin (DE)

(73) Assignee: Alcon Inc., Fribourg (CH)

( * ) Notice: Subject to any disclaimer, the term of this patent is extended or adjusted under 35 U.S.C. 154(b) by 936 days.

(21) Appl. No.: 17/501,929

(22) Filed: Oct. 14, 2021

(65) Prior Publication Data

US 2022/0183550 A1    Jun. 16, 2022

Related U.S. Application Data

(60) Provisional application No. 63/126,441, filed on Dec. 16, 2020.

(51) Int. Cl.
    *A61B 3/10*    (2006.01)
(52) U.S. Cl.
    CPC ............ *A61B 3/101* (2013.01); *A61B 3/1015* (2013.01); *A61B 3/102* (2013.01)
(58) Field of Classification Search
    CPC ....... A61B 3/101; A61B 3/1015; A61B 3/102; A61B 3/107; A61B 3/18; A61B 3/185; A61B 3/117; A61B 3/1173; A61B 3/1176; A61B 3/1208; A61B 3/1216; A61B 3/1225
    USPC ........................................................ 351/206
    See application file for complete search history.

(56) References Cited

U.S. PATENT DOCUMENTS

| | | | |
|---|---|---|---|
| 2013/0176532 A1* | 7/2013 | Sharma | A61B 3/102 351/246 |
| 2014/0228681 A1* | 8/2014 | Jia | G01B 9/02045 600/425 |
| 2016/0150952 A1* | 6/2016 | Raymond | A61B 3/1015 351/205 |
| 2018/0235460 A1 | 8/2018 | Neal et al. | |
| 2020/0113433 A1 | 4/2020 | Neal et al. | |

(Continued)

FOREIGN PATENT DOCUMENTS

JP    2018047083 A    3/2018

OTHER PUBLICATIONS

King-Smith P. Ewen et al: "Mechanisms, imaging and structure of tear film breakup", Ocular Surface, vol. 16, No. 1, Jan. 1, 2018 Jan. 1, 2018), pp. 4-30, XP055875752, ISSN: 1542-0124, DOI: 10. 1016/j . jtos .2017.09.007.

(Continued)

*Primary Examiner* — Travis S Fissel (57) ABSTRACT

In certain embodiments, an ophthalmic system for assessing a tear film of an eye comprises measuring devices and a computer. The measuring devices detect light reflected from the eye, where an ocular surface of the eye comprises the tear film, and generate data from the reflected light that describes the eye. The computer aligns the data corresponding to the same location for a plurality of locations, assesses the data at the locations to detect one or more abnormalities of the tear film, and determines a tear film description from the assessment of the data at the locations.

20 Claims, 5 Drawing Sheets

(56) References Cited

U.S. PATENT DOCUMENTS

2020/0359889 A1* 11/2020 Hogan .................. A61B 3/102

OTHER PUBLICATIONS

Bai Yuqiang et al: "Advances in thickness measurements and dynamic visualization of the tear film using non-invasive optical approaches", Progress in Retinal and Eye Research, Oxford, GB, vol. 58, Feb. 23, 2017 Feb. 23, 2017), pp. 28-44, X.P085029580, ISSN: 1350-9462, DOI: 10. 1016/J.PRETEYERES .2017.02.002.
Haixia Liu et al: "Measurement of the Time Course of Optical Quality and Visual Deterioration during Tear Break-Up", Investigative Opthalmology & Visual Science, vol. 51, No. 6, Jun. 1, 2010 (Jun. 1, 2010), p. 3318, XP055753667, US ISSN: 1552-5783, DOI: 10.1167/iovs.09-4831.

* cited by examiner

MULTI-DETECTOR ANALYSIS OF THE TEAR FILM OF AN EYE

TECHNICAL FIELD

The present disclosure relates generally to ophthalmic diagnostic systems, and more particularly to multi-detector analysis of the tear film of an eye.

BACKGROUND

The tear film on the anterior corneal surface of an eye is essential for the overall health of eyes. The tear film protects and lubricates the eyes, as well as washes away foreign particles. The film also reduces the risk of eye infection. Moreover, tear film conditions may influence certain medical treatments, e.g., may change the selection of an intraocular lens (IOL) used during a cataract treatment. Thus, assessing the tear film is important.

Certain devices can be used to perform a rudimentary screening of the tear film. For example, a user may evaluate images of Placido rings reflected from the cornea. Such screenings, however, are typically limited. Other devices may be dedicated to assessing tear film. However, these dedicated devices can be time consuming or difficult to use, and may require more invasive procedures, e.g., staining the surface of the eye prior to imaging.

BRIEF SUMMARY

In certain embodiments, an ophthalmic system for assessing a tear film of an eye comprises measuring devices and a computer. The measuring devices detect light reflected from the eye, where an ocular surface of the eye comprises the tear film, and generate data from the reflected light that describes the eye. The computer aligns the data corresponding to the same location for a plurality of locations, assesses the data at the locations to detect one or more abnormalities of the tear film, and determines a tear film description from the assessment of the data at the locations.

Embodiments may include none, one, some, or all of the following features:

The computer assesses the data at the locations by identifying a location where the data exhibits a lower signal-to-noise ratio than that of other locations, and detecting an abnormality comprising an inhomogeneity of the tear film at the location.

The computer assesses the data at the locations by identifying a location where the data exhibits a change in a signal-to-noise ratio, and detecting an abnormality comprising an instability of the tear film at the location.

The measuring devices comprise an optical coherence tomography (OCT) device that directs OCT light towards the eye, detects the OCT light reflected from the eye, and generates OCT data that describes the eye from the reflected OCT light. The computer may assess the data by identifying a location where the OCT data is missing data, and detecting an abnormality comprising an inhomogeneity of the tear film at the location. The computer may assess the data by determining an anterior corneal surface from the OCT data, determining a residual of the anterior corneal surface and the OCT data, and detecting an abnormality comprising an inhomogeneity of the tear film according to the residual. The computer may assess the data by identifying a location where a point distribution of the OCT data is changing, and detecting an abnormality comprising an inhomogeneity of the tear film at the location.

The measuring devices comprise an aberrometer that directs aberrometer light towards the eye, detects the aberrometer light reflected from the eye, and generates aberrometer data that describes the eye from the reflected aberrometer light. The computer may assess the data by determining a wavefront parameterization from the aberrometer data, determining a residual of the wavefront parameterization and the aberrometer data, and detecting an abnormality comprising an inhomogeneity of the tear film according to the residual. The computer may assess the data by identifying a location where a wavefront signal of the aberrometer data exhibits a change, and detecting an abnormality comprising an instability of the tear film at the location.

The measuring devices comprise a reflection topographer that directs topographer light comprising an illumination pattern towards the eye, detects the topographer light reflected from the eye, and generates topographer data that describes the eye from the reflected topographer light. The computer may assess the data by identifying a location where the topographer data is missing data, and detecting an abnormality comprising an inhomogeneity of the tear film at the location. The computer may assess the data by determining an anterior corneal surface from the topographer data, determining a residual of the anterior corneal surface and the topographer data, and detecting an abnormality comprising an inhomogeneity of the tear film according to the residual. The computer may assess the data by identifying a location where the illumination pattern exhibits a change, and detecting an abnormality comprising an instability of the tear film at the location.

The computer generates an image representing the description of the tear film, and outputs the image via a display. The image represents the ocular surface of the eye with graphical elements indicating the abnormalities of the tear film at the locations of the ocular surface.

In certain embodiments, an ophthalmic system for assessing a tear film of an eye comprises measuring devices and a computer. The measuring devices detect light reflected from the eye, where an ocular surface of the eye comprises the tear film, and generate data from the reflected light that describes the eye. The computer aligns the data corresponding to the same location for a plurality of locations, assesses the data at the locations to detect one or more abnormalities of the tear film, and determines a tear film description from the assessment of the data at the locations. The computer generates an image representing the description of the tear film, and outputs the image via a display. The image represents the ocular surface of the eye with graphical elements indicating the abnormalities of the tear film at the locations of the ocular surface.

Embodiments may include none, one, some, or all of the following features:

The image identifies a type of abnormality of the one or more abnormalities.

The image identifies one or more of the measuring devices that generated the data used to detect an abnormality of the one or more abnormalities.

In certain embodiments, an ophthalmic system for assessing a tear film of an eye comprises measuring devices and a computer. The measuring devices detect light reflected from the eye, where an ocular surface of the eye comprises the tear film, and generate data from the reflected light that describes the eye. The measuring devices comprise an optical coherence tomography (OCT) device, an aberrometer, and a reflection topographer. The OCT device directs OCT light towards the eye, detects the OCT light reflected from the eye, and generates OCT data that describes the eye from the reflected OCT light. The aberrometer directs aberrometer light towards the eye, detects the aberrometer light reflected from the eye, and generates aberrometer data that describes the eye from the reflected aberrometer light. The reflection topographer directs topographer light comprising an illumination pattern towards the eye, detects the topographer light reflected from the eye, and generates topographer data that describes the eye from the reflected topographer light. The computer aligns the data corresponding to the same location for a plurality of locations, and assesses the data at the locations to detect one or more abnormalities of the tear film. The computer assesses the data by: identifying a location where the data exhibits a lower signal-to-noise ratio than that of other locations, and detecting an abnormality comprising an inhomogeneity of the tear film at the location; identifying a location where the data exhibits a change in a signal-to-noise ratio, and detecting an abnormality comprising an instability of the tear film at the location; identifying a location where the OCT data is missing data, and detecting an abnormality comprising an inhomogeneity of the tear film at the location; determining an anterior corneal surface from the OCT data, determining a residual of the anterior corneal surface and the OCT data, and detecting an abnormality comprising an inhomogeneity of the tear film according to the residual; identifying a location where a point distribution of the OCT data is changing, and detecting an abnormality comprising an inhomogeneity of the tear film at the location; determining a wavefront parameterization from the aberrometer data, determining a residual of the wavefront parameterization and the aberrometer data, and detecting an abnormality comprising an inhomogeneity of the tear film according to the residual; identifying a location where a wavefront signal of the aberrometer data exhibits a change, and detecting an abnormality comprising an instability of the tear film at the location; identifying a location where the topographer data is missing data, and detecting an abnormality comprising an inhomogeneity of the tear film at the location; determining an anterior corneal surface from the topographer data, determining a residual of the anterior corneal surface and the topographer data, and detecting an abnormality comprising an inhomogeneity of the tear film according to the residual; and identifying a location where the illumination pattern exhibits a change, and detecting an abnormality comprising an instability of the tear film at the location. The computer determines a tear film description from the assessment of the data at the locations. The computer generates an image representing the description of the tear film and outputs the image via a display. The image represents the ocular surface of the eye with graphical elements indicating the abnormalities of the tear film at the locations of the ocular surface.

DESCRIPTION OF EXAMPLE EMBODIMENTS

Referring now to the description and drawings, example embodiments of the disclosed apparatuses, systems, and methods are shown in detail. The description and drawings are not intended to be exhaustive or otherwise limit the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments.

Embodiments of the system include multiple measuring devices, such as an optical coherence tomography (OCT) device, reflection topographer, and aberrometer. The measuring devices measure an ocular surface of the eye, which is the interface between the functioning eye and external environment and includes the tear film. The data is analyzed to provide an assessment of the tear film.

Figure 1:
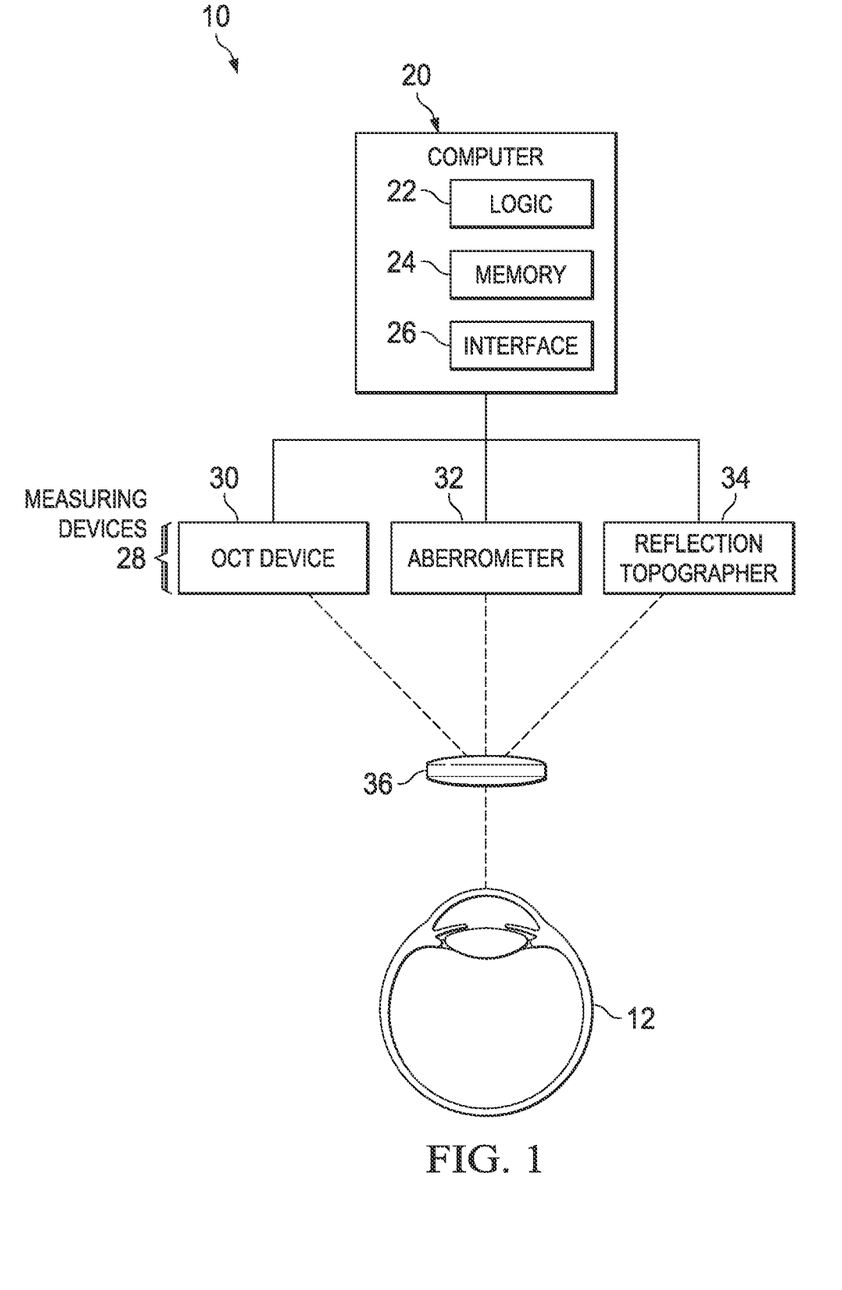
FIG. 1 illustrates an example of a system that assesses the tear film of an eye, according to certain embodiments.

FIG. 1 illustrates an example of a system 10 that assesses the tear film of an eye 12, according to certain embodiments. In the example, system 10 includes a computer 20 (which includes logic 22, a memory 24, and an interface 26), measuring devices 28, and an optical system 36, coupled as shown. Measuring devices 28 include an optical coherence tomography (OCT) device 30, an aberrometer 32, and a topographer 34, coupled as shown.

As an example overview, measuring devices 28 detect light reflected from eye 12 and generate data that describes eye 12 from the reflected light. Computer 20 aligns the data corresponding to the same locations of the ocular surface to assess the data at the locations. Computer 20 determines a description of the tear film from the assessment.

Turning to the parts of system 10, measuring devices 28 include OCT device 30, aberrometer 32, and topographer 34. OCT device 30 may be any suitable device that uses OCT to capture two- or three-dimensional images from within optical scattering media, e.g., eye tissue. OCT device 30 may use time domain, frequency domain, or other suitable spectral encoding, and may use single point, parallel, or other suitable scanning.

According to an example of operation, OCT device 30 directs OCT light towards eye 12 and detects the OCT light reflected from the parts of eye 12 to generate an image of the parts. OCT device 30 detects reflections from points of an interface between media, e.g., between the air and eye 12 or between parts of eye 12 (e.g., cornea, aqueous humor, lens, vitreous humor, and retina). For example, OCT device 30 detects reflections from points of the anterior corneal surface. OCT device 30 records the optical path lengths of the detected light and converts the lengths to distances to yield the distances to the points of the interface, which may be regarded as the point distribution of the interface. For example, OCT device 30 may yield the point distribution of the anterior corneal surface, which describes the shape of the surface. The point distributions for different interfaces of eye 12 may be used to create an ocular model. OCT device 30 may output OCT measurement data in any suitable manner, e.g., as distances, a point distribution, a topology, an ocular model, and/or a map.

Aberrometer 32 uses aberrometry (i.e., wavefront technology) to determine the aberrations of eye 12. As a wavefront of light travels through eye 12 and is reflected back through eye 12, aberrations of eye 12 distort the shape of the wavefront from an ideal shape. A Hartmann-Shack aberrometer is an example of aberrometer 32. According to an example of operation, aberrometer 32 directs aberrometer light towards eye 12 and detects the aberrometer light reflected from eye 12 to measure the shape of the wavefront. Aberrometer 32 generates measurement data that describe the deviations of the measured wavefront from the ideal wavefront. The aberrometer measurement data may be in the form of a wavefront map, a wavefront parameterization (e.g., Zernike parameterization), and/or mathematical functions (e.g., Zernike polynomials). Generally, aberrometer 32 provides measurements only in the pupil region.

Reflection topographer 34 measures the shape of the anterior corneal surface of eye 12 by detecting how the surface reflects an illumination pattern (e.g., concentric rings or grid of dots) projected onto the surface. If the surface is an ideal sphere, the reflected pattern matches the projected pattern. If the surface has aberrations, areas where the reflected portions of the pattern are closer together may indicate steeper corneal curvature, and areas where the portions are farther part may indicate flatter areas. Reflection topographer 34 typically includes an illumination system that projects the illumination pattern and a sensor (e.g., a camera) that detects the reflected light. According to an example of operation, reflection topographer 34 directs topographer light comprising the illumination pattern towards eye 12, and detects the topographer light reflected from eye 12. Topographer 34 may output topographer measurement data, such as a map of the surface, e.g., an axial, tangential, refractive power, or elevation map.

Measuring devices 28 may acquire measurements sequentially and/or simultaneously. The measurements from different devices 28 are aligned according to location (e.g., measurement data corresponding the same location of eye 12 are identified and evaluated) to determine what the different devices 28 measured at the same location. In certain embodiments, the data may be aligned using a feature of eye 12, e.g., the pupil or iris markings. In other embodiments, measuring devices 28 may take measurements along the same optical path such that eye 12 has the same alignment for the measurements.

Optical system 36 includes one or more optical elements that direct light from measuring devices 28 towards eye 12. An optical element can act on (e.g., transmit, reflect, refract, diffract, collimate, condition, shape, focus, modulate, and/or otherwise act on) a laser beam. Examples of optical elements include a lens, prism, mirror, diffractive optical element (DOE), holographic optical element (HOE), and spatial light modulator (SLM).

Computer 20 controls the operation of system 10 to assess the tear film of eye 12. To assess the tear film, computer 20 receives measurement data from measuring devices 28 and aligns the data corresponding to the same location for a plurality of locations of the ocular surface. Computer 20 then assesses the data to determine a tear film description. The data may indicate abnormalities of the tear film. Types of abnormalities include, e.g., an inhomogeneity or instability of the tear film. An inhomogeneity of the tear film may be a deviation from normal tear film, e.g., an area where the tear film is absent or abnormally thin, or where the chemical composition of the tear film is not normal. An instability of the tear film may be a change in the tear film, e.g., an area where the tear film changes from normal to abnormal.

In certain embodiments, computer 20 assesses measurement data according to the signal-to-noise ratio associated with the data. A measuring device 28 typically has an illumination source and a sensor (e.g., a camera). The illumination source directs light towards locations of the eye (e.g., the ocular surface). The sensor detects light reflected from the eye, generates a signal in response to detecting the light, and outputs measurement data according to the signal. The signal-to-noise ratio of data from a location is the ratio of the measured signal to the overall measured noise at the location. A higher signal-to-noise ratio typically indicates better quality data. A location with a lower or decreased signal-to-noise ratio may indicate an issue with the tear film, e.g., the tear film is missing.

In the embodiments, computer 20 may assess the data by identifying a location where the data exhibits a decreased signal-to-noise ratio, and determining the tear film has an inhomogeneity at the location. The decrease may be in the range of, e.g., a decrease greater than 10 to 20, 20 to 30, or 30 percent. In the embodiments, computer 20 may assess the data by identifying a location where the data exhibits a change in a signal-to-noise ratio, and determining the tear film has an instability at the location. The change may be in the range of, e.g., a change greater than 10 to 20, 20 to 30, or 30 percent.

In certain embodiments, computer 20 assesses measurement data according to the presence or absence of data. If data is missing at a location, there may be an inhomogeneity at the location. In certain embodiments, computer 20 assesses measurement data according to whether there is a change in the signal generated in response to detecting light that propagates through and is refracted by a certain area of the cornea, e.g., a wavefront signal generated by aberrometer 32. The change may indicate an instability at the location. The change may be in the range of, e.g., a change greater than 10 to 20, 20 to 30, or 30 percent.

In certain embodiments, computer 20 assesses measurement data by comparing the data from a measuring device 28 to other measurements. The other measurements may be made by a different measuring device 28 of system 10 or a measuring device 28 external to system 10. For example, OCT data may be compared to topographer data or to data made by a measuring device external to system 10.

In certain embodiments, computer 20 assesses measurement data from the residuals of parameterization of the data. In the embodiments, computer 20 may determine a mathematical function that describes a part of eye 12 by finding parameters of the function that most closely fits the measurement data. For example, computer 20 may determine the shape of the anterior corneal surface from parameterization of OCT data and/or topographer data. As another example, computer 20 may determine a wavefront parameterization from the aberrometer data. Computer 20 may then determine a residual that describes differences between the parameterization and the measurement data. A residual with an unexpected signature may indicate an abnormality of the tear film. For example, an unexpected signature of the residuals of a 6th order Zernike wavefront parameterization indicates smaller-scale structures, which typically occur on the cornea. This in turn may indicate an irregular tear film.

In certain embodiments, computer 20 assesses measurement data from specific measuring devices 28. For example, computer 20 assesses OCT data from OCT device 30. A point distribution of the OCT data may describe the anterior corneal surface. Changes at a location of the point distribution may indicate the tear film is changing at the location, i.e., the tear film has an instability at the surface. As another example, computer 20 assesses topographer data from reflection topographer 34. Changes at a location of the illumination pattern of the topographer data may indicate an instability of the tear film at the location.

Computer 20 determines the tear film description from the data assessment. Computer 20 may use data from one or more measuring devices 28 to describe the tear film at particular locations. In certain embodiments, computer 20 generates an image representing the description of the tear film, and outputs the image via a display. The image represents the ocular surface of the eye with one or more graphical elements indicating one or more tear film characteristics at the locations of the ocular surface. More details about the tear film description and image are described with reference to FIGS. 2A through 2C.

Figure 2A:
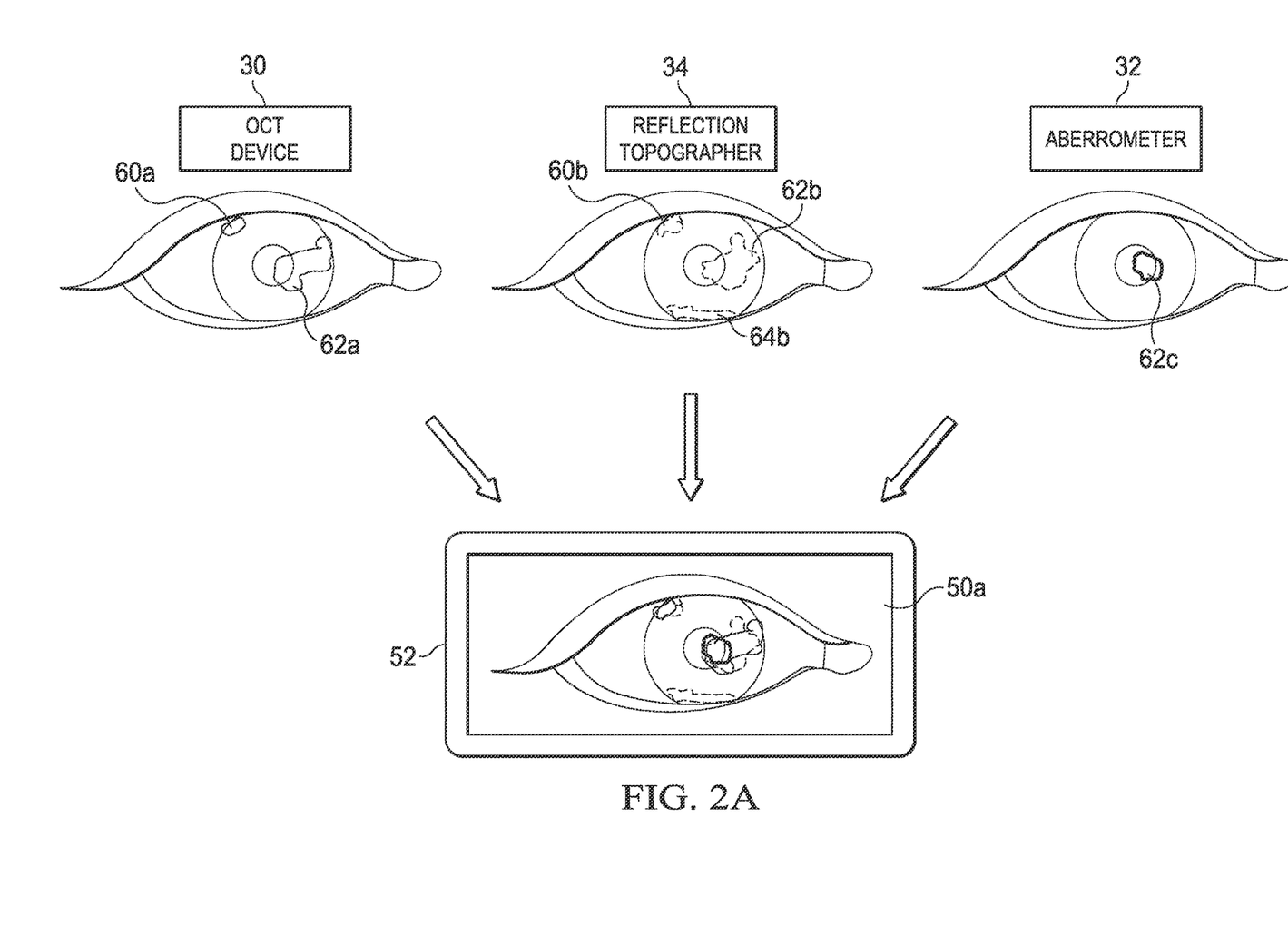
FIGS. 2A through 2C illustrate examples of the system of FIG. 1 generating an image of a tear film description.
Figure 2B:
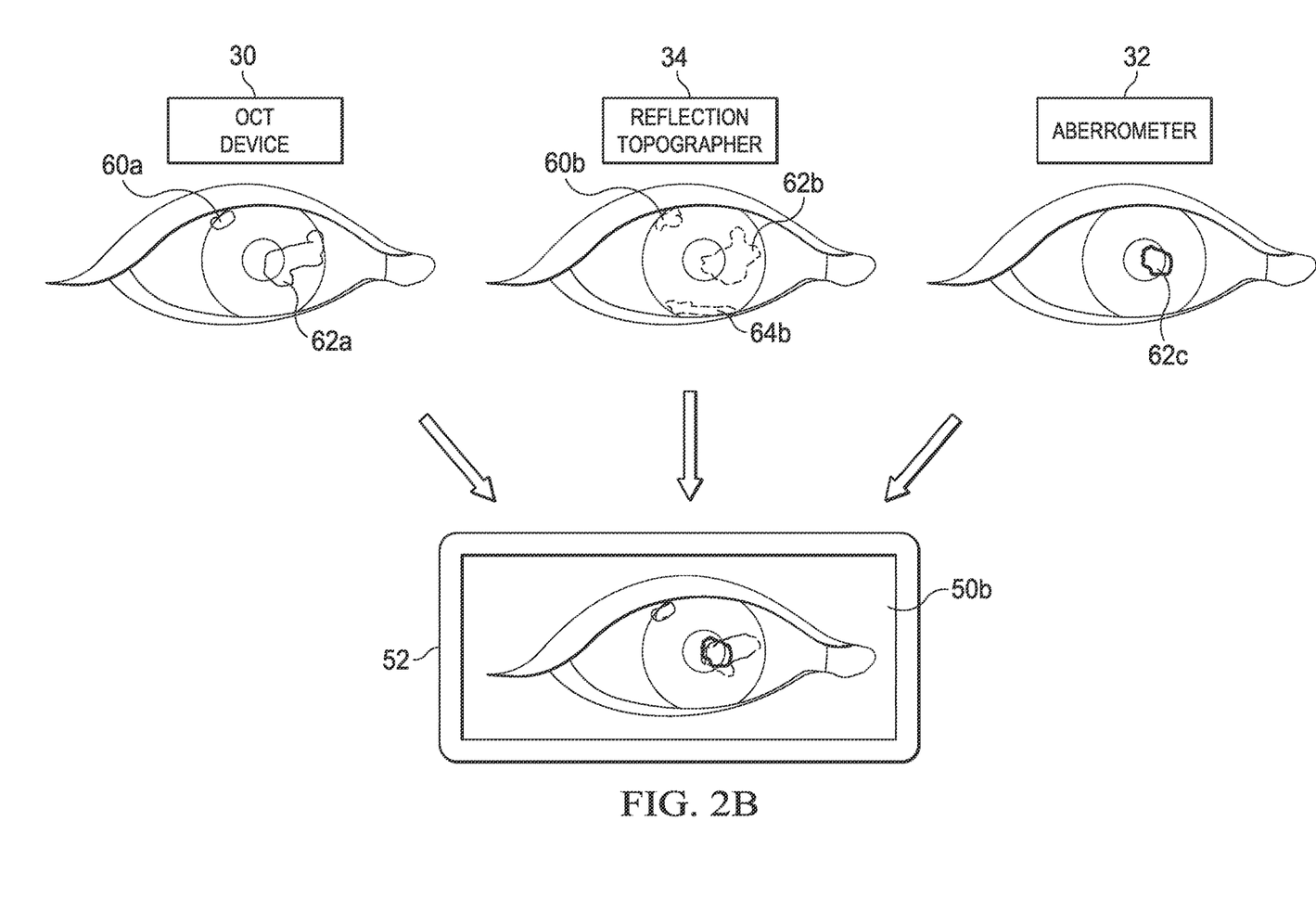
Figure 2C:
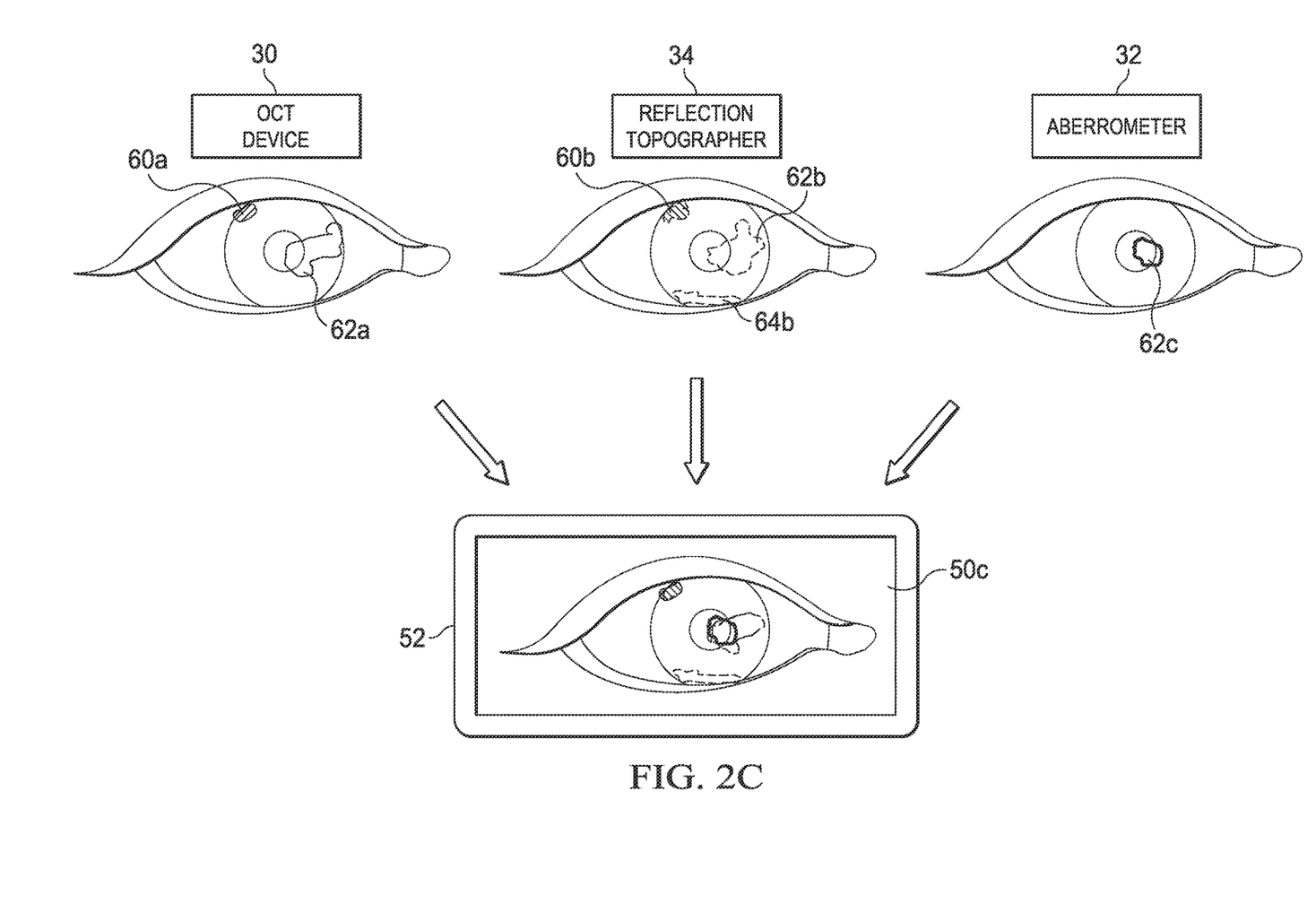

FIGS. 2A through 2C illustrate examples of system 10 generating an image 50 (50a, 50b, 50c) of a tear film description. In the examples, OCT device 30, aberrometer 32, and topographer 34 provide measurement data, computer 20 (not shown) generates image 50 from the data, and display 52 (which may be part of interface 26) displays image 50. OCT data shows tear abnormalities at regions 60a and 62a; aberrometer data shows tear abnormalities at regions 60b, 62b, and 64b; and topographer data shows tear abnormalities at region 62c. Regions 60 (60a, 60b) are substantially overlapping, as well as regions 62 (62a, 62b, 62c). Aberrometer 32 typically does not provide measurements outside of the pupil region, so region 62c does not extend outside of the pupil region.

An image 50 may include graphical user interface elements, or graphical elements, that describe the tear film. A graphical element may have any suitable property, e.g., size, shape, color, fill pattern, alphanumeric label, or other property. In certain embodiments, a graphical element may be overlaid onto an image of an eye, e.g., a photo or video of an eye or a graphical element that represents an eye. For example, in images 50a, 50b, 50c, graphical elements are overlaid onto an image of an eye to indicate the presence of a tear film abnormality at regions of the eye.

Computer 20 may include one, two or more, or all abnormalities detected by one, two or more, or all measuring devices 28 of system 10 in the tear film description. Generally, if measuring devices 28 agree on the presence an abnormality (e.g., inhomogeneity and/or instability) at a location, computer 20 includes the abnormality at the location in the description.

If measuring devices 28 disagree on the presence of an abnormality, computer 20 may include or exclude the abnormality. In certain embodiments, computer 20 may include the abnormality, and may identify which devices 28 detected the abnormality. For example, image 50a of FIG. 2A includes abnormalities from all measuring devices 28 of system 10, where abnormalities from OCT device 30 are shown with thin lines, from topographer 34 with dashed lines, and from aberrometer 32 with bold lines. In other embodiments, computer 20 may exclude the abnormality according to any suitable factor. Computer 20 may exclude an abnormality if a predefined minimum number of devices 28 required to detect the abnormality fail to detect the abnormality. For example, image 50b of FIG. 2B includes only abnormalities 64 detected by at least two devices 28, so omits abnormality 64b detected by only one device 28, i.e., topographer 34. Computer 20 may exclude an abnormality if a predefined device 28 required to detect the abnormality fails to detect the abnormality. For example, an abnormality may be required to be detected by OCT device 30, aberrometer 32, or topographer 34. Computer 20 may exclude an abnormality according to the detection quality (e.g., accuracy, precision, and/or reliability) of a device 28 at the abnormality location. For example, aberrometer 32 typically does not provide measurements outside of the pupil region, so if aberrometer 32 (and no other device 28) detects an abnormality outside of the pupil region, that abnormality may be regarded as an error.

In certain embodiments, computer 20 may combine abnormalities detected by different devices 28. Computer 20 may apply a function (e.g., an averaging function) to the abnormalities. For example, an abnormality for a device p may be given a detection value $v_p=1$, if device p detects the abnormality, and detection value $v_p=0$, if device p does not. An averaging function may be applied to find an average detection value $v_p$. Abnormalities with detection values that satisfy a minimum detection value (e.g., greater than 0.3, 0.5, or 0.7) may be included in the description. In certain embodiments, detection value $v_p$ may be modified according to any suitable factor, e.g., the certainty of the measurement and/or the detection quality of the device 28.

Computer 20 may describe the abnormalities in the tear film description in any suitable manner. In certain embodiments, a graphical element may indicate a region of the eye with an abnormality. For example, images 50a, 50b, 50c use lines to outline regions where abnormalities are located. In another example, the regions may be indicated by colors or fill patterns.

Computer 20 may include any suitable characteristic of the abnormalities in the tear film description using any suitable graphical element property. In certain embodiments, image 50 may identify the device 28 that detected an abnormality. For example, in images 50a, 50b, 50c, abnormalities from OCT device 30 are shown with thin lines, from topographer 34 with dashed lines, and from aberrometer 32 with bold lines. In certain embodiments, image 50 may identify the type of abnormalities. For example, in image 50c of FIG. 2C, regions 60 (60a, 60b) are shown with a fill pattern representing an instability. Regions 62 and 64 have no fill pattern, representing an inhomogeneity. In certain embodiments, an image 50 may indicate the confidence in the detection of an abnormality, which may represent the certainty of the measurement and/or the detection quality of the device 28. For example, anomalies with a higher confidence of detection may have a different color than anomalies with a lower confidence.

Figure 3:
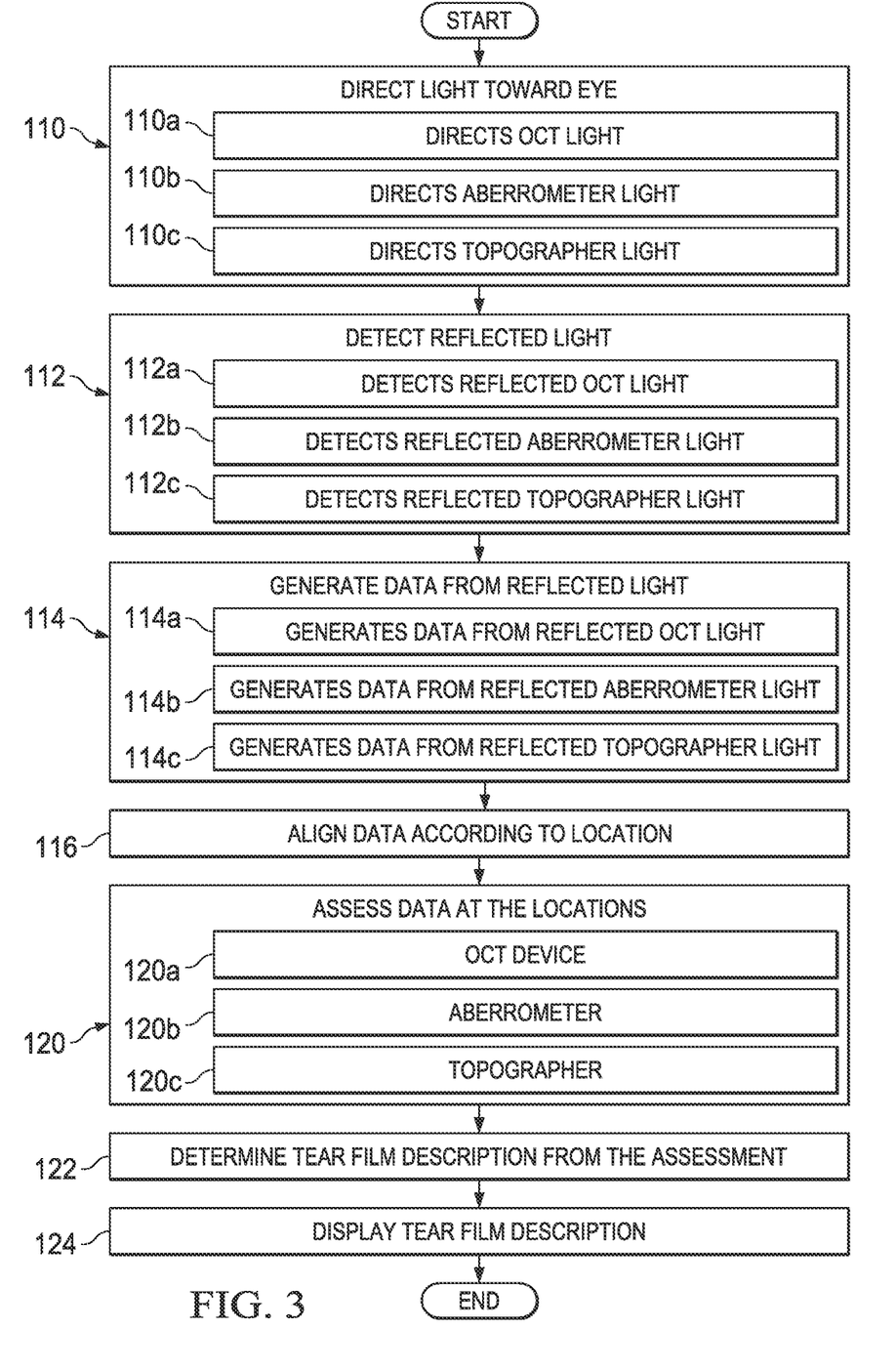
FIG. 3 illustrates an example of a method for assessing the tear film of an eye that may be performed by the system of FIG. 1, according to certain embodiments.

FIG. 3 illustrates an example of a method for assessing the tear film of an eye that may be performed by system 10, according to certain embodiments. Certain steps of the method may be performed by computer 20, which may send instructions to components of system 10 to perform certain operations. The method starts at step 110, where measuring devices 28 direct light towards eye 12. In certain embodiments, measuring devices 28 include, e.g., OCT device 30, aberrometer 32, and topographer 34. OCT device 30 directs OCT light at step 110a, aberrometer 32 directs aberrometer light at step 110b, and topographer 34 directs topographer light at step 110c.

Eye 12 reflects the light, and measuring devices 28 detect the reflected light at step 112. OCT device 30 detects reflected OCT light at step 112a, aberrometer 32 detects reflected aberrometer light at step 112b, and topographer 34 detects reflected topographer light at step 112c.

Measuring devices 28 generate data that describes eye 12 from the reflected light at step 114. OCT device 30 generates OCT data from reflected OCT light at step 114a, aberrometer 32 generates aberrometer data from reflected aberrometer light at step 114b, and topographer 34 generates topographer data from reflected topographer light at step 114c.

Computer 20 aligns the data from measuring devices 28 at step 116 according to location, and assesses the data at the locations at step 120. Computer 20 may assess the data in any suitable manner. For example, computer 20 may identify a location where the data exhibits a lower signal-to-noise ratio than that of other locations, and determine the tear film has an inhomogeneity at the location. As another example, computer 20 may identify a location where the data exhibits a change in a signal-to-noise ratio, and determine that the tear film has an instability at the location.

Computer 20 assesses the data from OCT device 30 at step 116a. For example, computer 20 may identify a location where the OCT data is missing data, and determine that the tear film has an inhomogeneity at the location. As another example, computer 20 may determine an anterior corneal surface from the OCT data, determine a residual of the anterior corneal surface and the OCT data, and determine that the tear film has an inhomogeneity according to the residual. As another example, computer 20 may identify a location where a point distribution of the OCT data is changing, and determine that the tear film has an instability at the location.

Computer 20 assesses the data from aberrometer 32 at step 116b. For example, computer 20 may determine a wavefront parameterization from the aberrometer data, determine a residual of the wavefront parameterization, and determine that the tear film has an inhomogeneity according to the residual. As another example, computer 20 may identify a location where a wavefront signal of the aberrometer data exhibits a change, and determine that the tear film has an instability at the location.

Computer 20 assesses the data from topographer 34 at step 116c. For example, computer 20 may identify a location where the topographer data is missing data, and determine that the tear film has an inhomogeneity at the location. As another example, computer 20 may determine an anterior corneal surface from the topographer data, determine a residual of the anterior corneal surface and the topographer data, and determine that the tear film has an inhomogeneity according to the residual. As another example, computer 20 may identify a location where an illumination pattern of the topographer data exhibits a change, and determine that the tear film has an instability at the location.

Computer 20 determines a tear film description from the assessment at step 122. Computer 20 may use data from one or more measuring devices 28 to describe the tear film at particular locations. Computer 20 displays the tear film description at step 124. In certain embodiments, computer 20 generates an image representing the tear film description, and outputs the image via a display. The image may show the ocular surface of the eye and may have graphical elements indicating tear film characteristics at regions of the ocular surface. The method then ends.

A component (such as the control computer) of the systems and apparatuses disclosed herein may include an interface, logic, and/or memory, any of which may include computer hardware and/or software. An interface can receive input to the component and/or send output from the component, and is typically used to exchange information between, e.g., software, hardware, peripheral devices, users, and combinations of these. A user interface (e.g., a Graphical User Interface (GUI)) is a type of interface that a user can utilize to interact with a computer. Examples of user interfaces include a display, touchscreen, keyboard, mouse, gesture sensor, microphone, and speakers.

Logic can perform operations of the component. Logic may include one or more electronic devices that process data, e.g., execute instructions to generate output from input. Examples of such an electronic device include a computer, processor, microprocessor (e.g., a Central Processing Unit (CPU)), and computer chip. Logic may include computer software that encodes instructions capable of being executed by the electronic device to perform operations. Examples of computer software include a computer program, application, and operating system.

A memory can store information and may comprise tangible, computer-readable, and/or computer-executable storage medium. Examples of memory include computer memory (e.g., Random Access Memory (RAM) or Read Only Memory (ROM)), mass storage media (e.g., a hard disk), removable storage media (e.g., a Compact Disk (CD) or Digital Video or Versatile Disk (DVD)), database, network storage (e.g., a server), and/or other computer-readable media. Particular embodiments may be directed to memory encoded with computer software.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, or the operations of the systems and apparatuses may be performed by more, fewer, or other components, as apparent to those skilled in the art. As another example, modifications may be made to the methods disclosed herein. The methods may include more, fewer, or other steps, and the steps may be performed in any suitable order, as apparent to those skilled in the art.

To aid the Patent Office and readers in interpreting the claims, Applicants note that they do not intend any of the claims or claim elements to invoke 35 U.S.C. § 112(f), unless the words "means for" or "step for" are explicitly used in the particular claim. Use of any other term (e.g., "mechanism," "module," "device," "unit," "component," "element," "member," "apparatus," "machine," "system," "processor," or "controller") within a claim is understood by the applicants to refer to structures known to those skilled in the relevant art and is not intended to invoke 35 U.S.C. § 112(f).

What is claimed:

1. An ophthalmic system for assessing a tear film of an eye, the system comprising:
 a plurality of measuring devices, each measuring device configured to:
  detect light reflected from the eye, an ocular surface of the eye comprising the tear film; and
  generate data that describes the eye from the reflected light; and
 a computer configured to:
  for each location of a plurality of locations of the ocular surface, align the data corresponding to the same location;
  assess the data at the plurality of locations to detect one or more abnormalities of the tear film by:
   identifying a location where the data exhibits a lower signal-to-noise ratio than that of other locations; and
   detecting an abnormality comprising an inhomogeneity of the tear film at the location where the data exhibits the lower signal-to-noise ratio; and determine a tear film description from the assessment of the data at the plurality of locations.

2. The ophthalmic system of claim 1, a measuring device of the plurality of measuring devices comprising an optical coherence tomography (OCT) device configured to:
direct OCT light towards the eye;
detect the OCT light reflected from the eye; and
generate OCT data that describes the eye from the reflected OCT light.

3. The ophthalmic system of claim 2, the computer further configured to assess the data at the plurality of locations by:
identifying a location where the OCT data is missing data; and
detecting an abnormality comprising an inhomogeneity of the tear film at the location.

4. The ophthalmic system of claim 2, the computer further configured to assess the data at the plurality of locations by:
determining an anterior corneal surface from the OCT data;
determining a residual of the anterior corneal surface and the OCT data; and
detecting an abnormality comprising an inhomogeneity of the tear film according to the residual.

5. The ophthalmic system of claim 2, the computer further configured to assess the data at the plurality of locations by:
identifying a location where a point distribution of the OCT data is changing; and
detecting an abnormality comprising an inhomogeneity of the tear film at the location.

6. The ophthalmic system of claim 1, a measuring device of the plurality of measuring devices comprising an aberrometer configured to:
direct aberrometer light towards the eye;
detect the aberrometer light reflected from the eye; and
generate aberrometer data that describes the eye from the reflected aberrometer light.

7. The ophthalmic system of claim 6, the computer further configured to assess the data at the plurality of locations by:
determining a wavefront parameterization from the aberrometer data;
determining a residual of the wavefront parameterization and the aberrometer data; and
detecting an abnormality comprising an inhomogeneity of the tear film according to the residual.

8. The ophthalmic system of claim 6, the computer further configured to assess the data at the plurality of locations by:
identifying a location where a wavefront signal of the aberrometer data exhibits a change; and
detecting an abnormality comprising an instability of the tear film at the location.

9. The ophthalmic system of claim 1, a measuring device of the plurality of measuring devices comprising a reflection topographer configured to:
direct topographer light comprising an illumination pattern towards the eye;
detect the topographer light reflected from the eye; and
generate topographer data that describes the eye from the reflected topographer light.

10. The ophthalmic system of claim 9, the computer further configured to assess the data at the plurality of locations by:
identifying a location where the topographer data is missing data; and
detecting an abnormality comprising an inhomogeneity of the tear film at the location.

11. The ophthalmic system of claim 9, the computer further configured to assess the data at the plurality of locations by:
determining an anterior corneal surface from the topographer data;
determining a residual of the anterior corneal surface and the topographer data; and
detecting an abnormality comprising an inhomogeneity of the tear film according to the residual.

12. The ophthalmic system of claim 9, the computer further configured to assess the data at the plurality of locations by:
identifying a location where the illumination pattern exhibits a change; and
detecting an abnormality comprising an instability of the tear film at the location.

13. The ophthalmic system of claim 1, the computer further configured to:
generate an image representing the description of the tear film; and
output the image via a display.

14. The ophthalmic system of claim 13, the image representing the ocular surface of the eye with one or more graphical elements indicating the one or more abnormalities of the tear film at the locations of the ocular surface.

15. An ophthalmic system for assessing a tear film of an eye, the system comprising:
a plurality of measuring devices, each measuring device configured to:
detect light reflected from the eye, an ocular surface of the eye comprising the tear film; and
generate data that describes the eye from the reflected light; and
a computer configured to:
for each location of a plurality of locations of the ocular surface, align the data corresponding to the same location;
assess the data at the plurality of locations to detect one or more abnormalities of the tear film by:
identifying a location where the data exhibits a change in a signal-to-noise ratio; and
detecting an abnormality comprising an instability of the tear film at the location where the data exhibits the change in the signal-to-noise ratio; and
determine a tear film description from the assessment of the data at the plurality of locations.

16. An ophthalmic system for assessing a tear film of an eye, the system comprising:
a plurality of measuring devices, each measuring device configured to:
detect light reflected from the eye, an ocular surface of the eye comprising the tear film; and
generate data that describes the eye from the reflected light; and
a computer configured to:
for each location of a plurality of locations of the ocular surface, align the data corresponding to the same location;
assess the data at the plurality of locations to detect one or more abnormalities of the tear film by:
identifying a location where the data exhibits a lower signal-to-noise ratio than that of other locations; and
detecting an abnormality comprising an inhomogeneity of the tear film at the location where the data exhibits the lower signal-to-noise ratio;

determine a tear film description from the assessment of the data at the plurality of locations; and
generate and output an image representing the description of the tear film, the image representing the ocular surface of the eye with one or more graphical elements indicating the one or more abnormalities of the tear film at the locations of the ocular surface.

17. The ophthalmic system of claim 16, the image identifying a type of abnormality of the one or more abnormalities.

18. The ophthalmic system of claim 16, the image identifying one or more of the plurality of measuring devices that generated the data used to detect an abnormality of the one or more abnormalities.

19. An ophthalmic system for assessing a tear film of an eye, the system comprising:
a plurality of measuring devices, each measuring device configured to:
  detect light reflected from the eye, an ocular surface of the eye comprising the tear film; and
  generate data that describes the eye from the reflected light;
the plurality of measuring devices comprising:
  an optical coherence tomography (OCT) device configured to direct OCT light towards the eye, detect the OCT light reflected from the eye, and generate OCT data that describes the eye from the reflected OCT light;
  an aberrometer configured to direct aberrometer light towards the eye, detect the aberrometer light reflected from the eye, and generate aberrometer data that describes the eye from the reflected aberrometer light; and
  a reflection topographer configured to direct topographer light comprising an illumination pattern towards the eye, detect the topographer light reflected from the eye, and generate topographer data that describes the eye from the reflected topographer light; and
a computer configured to:
  for each location of a plurality of locations of the ocular surface, align the data corresponding to the same location;
  assess the data at the plurality of locations to detect one or more abnormalities of the tear film by:
    identifying a location where the data exhibits a lower signal-to-noise ratio than that of other locations, and detecting an abnormality comprising an inhomogeneity of the tear film at the location;
    identifying a location where the data exhibits a change in a signal-to-noise ratio, and detecting an abnormality comprising an instability of the tear film at the location;
    identifying a location where the OCT data is missing data, and detecting an abnormality comprising an inhomogeneity of the tear film at the location;
    determining an anterior corneal surface from the OCT data, determining a residual of the anterior corneal surface and the OCT data, and detecting an abnormality comprising an inhomogeneity of the tear film according to the residual;
    identifying a location where a point distribution of the OCT data is changing, and detecting an abnormality comprising an inhomogeneity of the tear film at the location;
    determining a wavefront parameterization from the aberrometer data, determining a residual of the wavefront parameterization and the aberrometer data, and detecting an abnormality comprising an inhomogeneity of the tear film according to the residual;
    identifying a location where a wavefront signal of the aberrometer data exhibits a change, and detecting an abnormality comprising an instability of the tear film at the location;
    identifying a location where the topographer data is missing data, and detecting an abnormality comprising an inhomogeneity of the tear film at the location;
    determining an anterior corneal surface from the topographer data, determining a residual of the anterior corneal surface and the topographer data, and detecting an abnormality comprising an inhomogeneity of the tear film according to the residual; and
    identifying a location where the illumination pattern exhibits a change, and detecting an abnormality comprising an instability of the tear film at the location;
  determine a tear film description from the assessment of the data at the plurality of locations; and
  generate an image representing the description of the tear film and output the image via a display, the image representing the ocular surface of the eye with one or more graphical elements indicating the one or more abnormalities of the tear film at the locations of the ocular surface.

20. An ophthalmic system for assessing a tear film of an eye, the system comprising:
a plurality of measuring devices, each measuring device configured to:
  detect light reflected from the eye, an ocular surface of the eye comprising the tear film; and
  generate data that describes the eye from the reflected light; and
a computer configured to:
  for each location of a plurality of locations of the ocular surface, align the data corresponding to the same location;
  assess the data at the plurality of locations to detect one or more abnormalities of the tear film by:
    identifying a location where the data is missing; and
    detecting an abnormality comprising an inhomogeneity of the tear film at the location where the data is missing; and
  determine a tear film description from the assessment of the data at the plurality of locations.

* * * * *